United States Patent
Kii et al.

(10) Patent No.: US 9,779,501 B2
(45) Date of Patent: *Oct. 3, 2017

(54) IMAGE PROCESSING APPARATUS, METHOD, AND PROGRAM

(71) Applicant: NIKON CORPORATION, Tokyo (JP)

(72) Inventors: Hiroaki Kii, Kawasaki (JP); Chisako Iwamoto, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,225

(22) Filed: Jan. 27, 2016

(65) Prior Publication Data

US 2016/0140710 A1    May 19, 2016

Related U.S. Application Data

(63) Continuation of application No. 14/103,040, filed on Dec. 11, 2013, now Pat. No. 9,280,698, which is a
(Continued)

(30) Foreign Application Priority Data

Jun. 20, 2011 (JP) .................................. 2011-135959

(51) Int. Cl.
*G06K 9/00* (2006.01)
*G06T 7/00* (2017.01)
(Continued)

(52) U.S. Cl.
CPC ........ *G06T 7/0012* (2013.01); *G06K 9/00127* (2013.01); *G06K 9/52* (2013.01);
(Continued)

(58) Field of Classification Search
CPC ................ G06K 9/00; G06T 1/00; G06T 7/00
(Continued)

(56) References Cited

U.S. PATENT DOCUMENTS

| 5,134,662 A * | 7/1992 | Bacus | G01N 15/1468 |
| | | | 348/79 |
| 7,555,161 B2 * | 6/2009 | Haddon | G06T 7/0012 |
| | | | 381/171 |

(Continued)

FOREIGN PATENT DOCUMENTS

| JP | 2003-500664 A | 1/2003 |
| JP | 2006-505782 A | 2/2006 |
| JP | 2010-527007 A | 8/2010 |
| JP | 2010-248094 A | 11/2010 |
| WO | 00/72258 A2 | 11/2000 |

OTHER PUBLICATIONS

Koshino, "Cell Motility and Localization of Signal transduction Protein (p125FAK) Relate to Extracellular Matrices in Human Melanoma Cell Line,"The Journal of the Iwate Medical Association, Aug. 1996, vol. 48, No. 3, pp. 261-272 (with translation).
(Continued)

*Primary Examiner* — Abolfazl Tabatabai
(74) *Attorney, Agent, or Firm* — Oliff PLC

(57) ABSTRACT

An image processing apparatus, a method, and a program for allowing cells to be quantitatively observed. A computer obtains a cell membrane image obtained by performing fluorescent observation on a cell membrane of a cell serving as a sample and a tricellular tight junction (tTJ) image obtained by performing fluorescent observation on a protein localized in a tTJ of the cell. The computer derives the size of area of a region of the cell by identifying the region of each cell from the cell membrane image, derives the size of area of the region of the protein localized in the cell from the tTJ image, and dividing the obtained size of area of the region of the protein by the size of area of the region of the cell, thus calculating an index of adhesion strength of the cells. The invention can be applied to an observation system.

42 Claims, 8 Drawing Sheets

Related U.S. Application Data continuation of application No. PCT/JP2012/065684, filed on Jun. 20, 2012.

(51) Int. Cl.

| | | |
|---|---|---|
| *G06K 9/52* | (2006.01) | |
| *G06T 7/62* | (2017.01) | |
| *G01V 3/00* | (2006.01) | |
| *G01N 21/64* | (2006.01) | |
| *G06K 9/46* | (2006.01) | |

(52) U.S. Cl.
CPC ............ *G06T 7/62* (2017.01); *G01N 21/6458* (2013.01); *G06K 2009/4666* (2013.01); *G06T 2207/10056* (2013.01); *G06T 2207/20036* (2013.01); *G06T 2207/30024* (2013.01)

(58) Field of Classification Search
USPC .......................... 382/128–134; 324/306, 309
See application file for complete search history.

(56) References Cited

U.S. PATENT DOCUMENTS 9,280,698 B2 *  3/2016  Kll ........................ G06T 7/0012
2010/0128961 A1    5/2010  Kalusche

OTHER PUBLICATIONS

Furuse, "Mechanism for Regulating Epithelial Permeability by Tight Junction with Intercellular Junction,"The 55th Lecture Congress of the Japan Salivary Gland Society, Nov. 10, 2010, vol. 51, pp. 10-11 (with translation).
International Search Report issued in International Patent Application No. PCT/JP2012/065684 dated Sep. 25, 2012 (with translation).
Written Opinion issued in International Patent Application No. PCT/JP2012/065684 dated Sep. 25, 2012.
Oct. 23, 2015 Office Action issued in U.S. Appl. No. 14/103,040.
Mar. 24, 2015 Office Action issued in U.S. Appl. No. 14/103,040.

\* cited by examiner

IMAGE PROCESSING APPARATUS, METHOD, AND PROGRAM

This is a Continuation of application Ser. No. 14/103,040 filed Dec. 11, 2013 (now U.S. Pat. No. 9,280,698), which in turn is a continuation of PCT/JP2012/065684 filed Jun. 20, 2012, which claims foreign priority to JP 2011-135959 filed Jun. 20, 2011. The disclosures of the prior applications are hereby incorporated by reference herein in their entirety.

TECHNICAL FIELD

The present invention relates to an image processing apparatus, a method, and a program for allowing cells to be quantitatively observed.

BACKGROUND ART

In general, various genes are related to human diseases and conditions, and in particular, for diseases of which cause is unknown, a method for finding related genes by using a technique such as gene screening method for knocking out the function of the related genes under many conditions and solving the diseases is sought for.

The effect of medicine in such screening is known to appear most significantly in change of localization of protein in a cell. Therefore, a method for quantitatively evaluating localization of protein according to individual screening is sought for, and for example, high content screening systems for performing analysis from fluorescence microscope images of cells have been developed.

In order to perform such screening, it is necessary to take an image of a culture vessel capable of cultivation under many conditions such as a microwell plate. An apparatus integrally including a microscope and analysis software is also known (for example, see Patent Literature 1). In high content screening performed by this apparatus, in a region of a cell nucleus which is segmented in image processing, a designated region centered at a predetermined point is adopted as a region of analysis target, which is analyzed.

By the way, a living body is divided into various sections by epitheliums, and a cell adhesion structure existing in each section has a barrier function for controlling passage of substance between cells and organs. The cell adhesion structure is important for maintaining a form of organs such as blood vessels, and is also useful for maintaining the environment in the ecology.

The abnormality of the barrier function may cause various diseases concerning skin, liver, kidney, and the like, and it has been revealed that it is also related to invasion of cancer and passage of white blood cells, and clarifying the mechanism of the cell adhesion structure is attracting attention.

With recent studies, protein condensed in tTJ (tricellular tight junction) which is a portion where three cells are in contact with each other has been discovered, and it is suggested that this plays an important role in the intensity of cell adhesion. For example, the protein condensed in tTJ includes tricellulin, LSR (Lipolysis stimulated lipoprotein receptor), and the like.

It is desired to find the detailed function of the protein condensed in such tTJ and develop evaluation method. More specifically, for example, a method and the like is desired to quantitatively evaluate the phenomenon that the intensity of cell adhesion is reduced because of changes of the localization of the protein existing in tTJ by causing medicine to take effect.

CITATION LIST

Patent Literature

Patent Literature 1: JP 2010-527007 W

SUMMARY OF INVENTION

Technical Problem

However, with the above technique, it used to be difficult to quantitatively observe a cell of observation target such as adhesion of the cell and localization of protein condensed in tTJ. For example, with the technique disclosed in Patent Literature 1, it is impossible to evaluate localization of complicated protein such as protein related to cell adhesion, and therefore, there was no choice but to determine the effect of medicine with the eyes of a person.

The present invention is made in view of such circumstances, and enables a cell to be quantitatively observed.

Solution to Problem

An image processing apparatus of the present invention includes first image processing means configured to identify, on the basis of a first observation image indicating localization of a protein related to a predetermined feature of a cell of observation target, a region of the protein in the first observation image, and calculation means configured to calculate, on the basis of quantitative information related to the region of the protein identified, an index representing the feature.

Advantageous Effects of Invention

According to the present invention, a cell can be quantitatively observed.

DESCRIPTION OF EMBODIMENTS

Hereinafter, an embodiment to which the present invention is applied will be explained with reference to drawings.

[Example of Configuration of Observation System]

Figure 1:
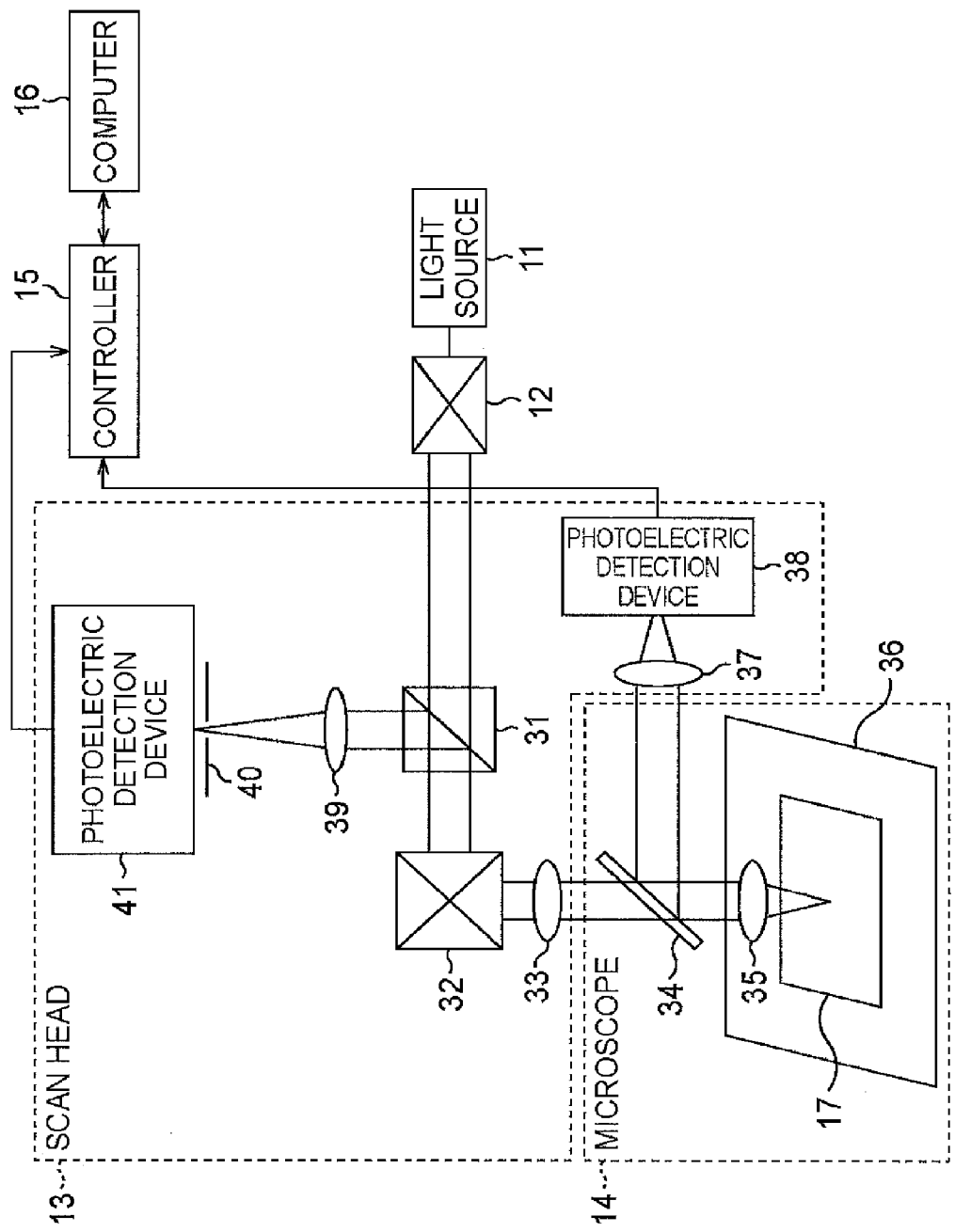
FIG. 1 is a figure illustrating an example of configuration of an embodiment of an observation system to which the present invention is applied.

FIG. 1 is a figure illustrating an example of configuration of an embodiment of an observation system to which the present invention is applied.

This observation system is to quantitatively observe a cell of observation target. Hereinafter, for example, explanation will continue in a case where epithelium cells of a living body are observation target, and adhesion strength of the cells is quantitatively observed.

In this case, the observation system is a screening system for performing analysis for determining the strength of adhesion of the cells, and in the screening, the index of cell adhesion strength of each cell is calculated from an image obtained by visualizing the cell adhesion molecules.

The observation system of FIG. 1 includes a light source 11, a beam expander 12, a scan head 13, a microscope 14, a controller 15, and a computer 16, and a sample 17 as observation target is observed with fluorescence by the observation system. In this case, the sample 17 is epithelium cells. Multiple epithelium cells are put in a container such as a microwell plate, and observed.

In the observation system, the scan head 13 for scanning light is attached to the microscope 14. The scan head 13 and the microscope 14 function as a two-photon microscope-attached confocal microscope (hereinafter simply referred to as confocal microscope). More specifically, this confocal microscope realizes confocal observation based on ordinary one-photon excitation method and observation based on two-photon excitation method.

The light source 11 emits illumination light (excitation light) to irradiate the sample 17 as observation target. For example, when the sample 17 is observed according to the two-photon excitation method, a short pulsed laser light source and the like is used as the light source 11.

The illumination light which is emitted from the light source 11 is shaped by the beam expander 12 so that the beam diameter is enlarged, and made into parallel light beam, which is incident upon the scan head 13.

The illumination light which has been led to the scan head 13 by space propagation as described above is incident upon the microscope 14 via the dichroic mirror 31, scan unit 32, and relay lens 33 provided in the scan head 13. Then, the sample 17 placed on the stage 36 is irradiated with the illumination light incident upon the microscope 14 via the dichroic mirror 34 and the object lens 35 in the microscope 14.

At this occasion, the scan unit 32 deflects the illumination light incident from the dichroic mirror 31 in the horizontal and depthwise direction in the figure, thus scanning the illumination light on the sample 17. When the sample 17 is irradiated with the illumination light, fluorescence which becomes the observation light is generated from the sample 17, and this fluorescence is incident upon the dichroic mirror 34 via the object lens 35.

In the case of two-photon excitation method, the fluorescence is generated only in proximity to the focal point, and high spatial resolution is provided by itself, and no pinhole is necessary. Therefore, in order to detect fluorescence with a high degree of efficiency, a detection device can be configured to be provided at a position as close to the sample as possible.

In such configuration, the dichroic mirror 34 reflects the fluorescence from the object lens 35 as necessary, so that it is incident upon the condensing lens 37. More specifically, the dichroic mirror 34 is configured to move physically, and when the fluorescence generated from the sample 17 by the two-photon excitation method is observed, the dichroic mirror 34 is arranged in an optical path of the illumination light (detection subject optical path), and when the fluorescence is observed with confocal method by ordinary one-photon excitation method, it is not arranged in the detection subject optical path.

When the dichroic mirror 34 is arranged in the detection subject optical path, the dichroic mirror 34 transmits the illumination light from the relay lens 33, and reflects the fluorescence from the sample 17, so that it is incident upon the condensing lens 37.

The fluorescence incident upon the condensing lens 37 is condensed by the condensing lens 37, and is received by the photoelectric detection device 38. The photoelectric detection device 38 performs photoelectric conversion on the received fluorescence. Then, an electric signal obtained from the photoelectric conversion is provided to the computer 16 from the photoelectric detection device 38 via the controller 15.

On the other hand, when the dichroic mirror 34 is not arranged in the detection subject optical path, the sample 17 is irradiated with the illumination light from the relay lens 33 via the object lens 35. Then, the fluorescence from the sample 17 passes the optical path of the illumination light in the opposite direction and is incident upon the dichroic mirror 31. More specifically, the fluorescence incident upon the object lens 35 from the sample 17 is incident upon the dichroic mirror 31 via the relay lens 33 and the scan unit 32.

The dichroic mirror 31 reflects the fluorescence from the scan unit 32 and it is incident upon the condensing lens 39. This dichroic mirror 31 passes the light having the wavelength of the illumination light, and reflects the light having the wavelength of the fluorescence.

The fluorescence incident upon the condensing lens 39 from the dichroic mirror 31 is condensed by the condensing lens 39, and passes through a pinhole provided in a confocal diaphragm 40, and is received by the photoelectric detection device 41. Then, the electric signal obtained by performing photoelectric conversion on the fluorescence received by the photoelectric detection device 41 is provided from the photoelectric detection device 41 via the controller 15 to the computer 16.

As described above, in the case of the confocal observation according to the one-photon excitation method, the fluorescence takes the passage from the object lens 35 to the photoelectric detection device 41. In the case of the observation according to the two-photon excitation method, detection can be done based on this passage by opening the pinhole. Hereinafter, for example, explanation will continue in a case where the sample 17 is observed according to the two-photon excitation method.

On the basis of the electric signal provided from the photoelectric detection device 41 or the photoelectric detection device 38 via the controller 15, the computer 16 generates an image of the sample 17, and on the basis of the generated image, the computer 16 calculates an index AD of adhesion strength of the cells for the sample 17.

For example, the observation system takes an image obtained by performing fluorescent observation on protein (X) localized at a cell membrane of a cell serving as the sample 17 (hereinafter referred to as cell membrane image) and an image obtained by performing fluorescent observation on protein (Y) localized at tTJ of the cells (hereinafter referred to as tTJ image). Then, on the basis of the cell membrane image and the tTJ image, the index AD of the adhesion strength of the cells is calculated.

[Example of Configuration of Computer]

Figure 2:
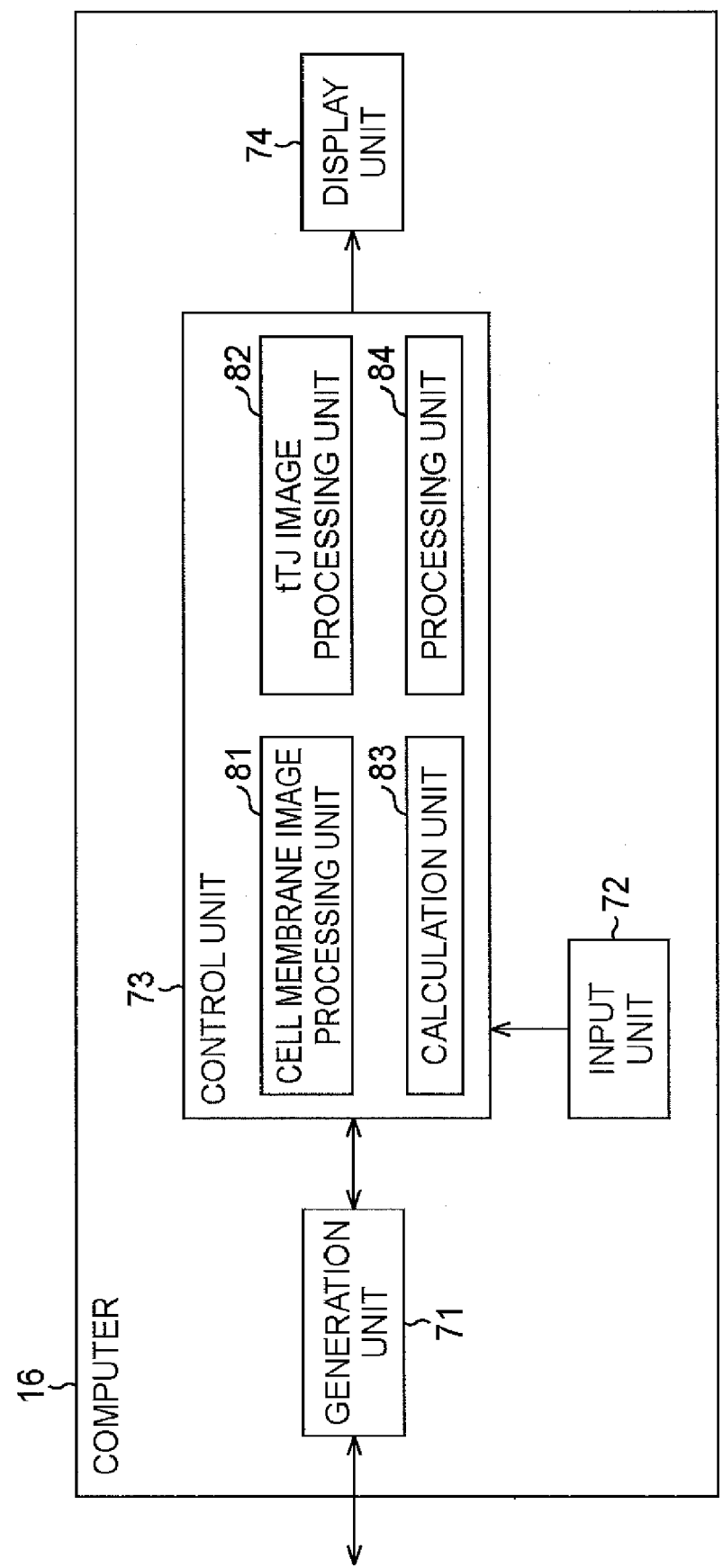
FIG. 2 is a figure illustrating an example of configuration of a computer.

More specifically, the computer 16 of FIG. 1 is configured as shown in FIG. 2. That is, the computer 16 includes a generation unit 71, an input unit 72, a control unit 73, and a display unit 74.

The generation unit 71 controls operation of the scan head 13, and on the basis of the electric signal provided from the photoelectric detection device 38 or the photoelectric detection device 41, the generation unit 71 generates the cell membrane image and the tTJ image, and provides them to the control unit 73. The input unit 72 is constituted by a mouse, buttons, and the like, and provides the control unit 73 with a signal according to user's operation.

The control unit 73 controls overall operation of the computer 16 in accordance with the signal provided from the input unit 72. The control unit 73 includes a cell membrane image processing unit 81, a tTJ image processing unit 82, a calculation unit 83, and a processing unit 84.

The cell membrane image processing unit 81 generates, as cell analysis information, information about the cells such as the number of cells included in the cell membrane image and the size of area of each cell from the cell membrane image provided from the generation unit 71. The tTJ image processing unit 82 derives the size of area of the protein (Y) localized in the tTJ in the cell from the tTJ image provided from the generation unit 71.

The calculation unit 83 calculates the index AD of the adhesion strength of the cells on the basis of the size of area of the protein (Y) localized in the tTJ of the cells and the cell analysis information. The processing unit 84 processes the index AD as necessary, provides it to the display unit 74, and displays it thereon. The display unit 74 is constituted by, for example, a liquid crystal display panel and the like, and displays the image and the like provided by the control unit 73.

[Explanation about Operation of Observation System]

Subsequently, operation of the observation system of FIG. 1 will be explained.

For example, when the sample 17 is observed, the epithelium cells are put in a container such as a microwell plate as the sample 17, and different medicine is added to each well containing the epithelium cells. For example, different siRNA (genes inhibiting generation of kinase (enzyme)) is added as medicine to each well, whereby samples having different observation conditions for each of the wells are prepared, e.g., the state where various kinds of kinases are knocked out (state where it is impossible to generate various kinds of kinases required for phosphorylation of various kinds of proteins). Then, in each well, the cells are observed by fluorescence, whereby the effect of the medicine is determined.

Such epithelium cells are prepared as the sample 17 and placed on the stage 36, and when the user commands start of observation of the epithelium cells, the observation system starts the observation processing, and performs the fluorescent observation of the sample 17. Hereinafter, the observation processing by the observation system will be explained with reference to the flowchart of FIG. 3.

In step S11, the generation unit 71 obtains the cell membrane image in accordance with the control of the control unit 73.

More specifically, the light source 11 emits illumination light. For example, the illumination light is light having a wavelength enabling fluorescent observation of the protein (X) localized in the cell membrane of the cells of the observation target. The illumination light emitted from the light source 11 passes through the beam expander 12, and through the dichroic mirror 31 to the object lens 35, and the sample 17 is irradiated with the illumination light. At this occasion, the scan unit 32 deflects the illumination light, so that the illumination light is scanned on the sample 17.

Accordingly, fluorescence is emitted from the protein (X) localized in the cell membrane of the sample 17, and the fluorescence is incident upon on the dichroic mirror 34 via the object lens 35, and further, after it is reflected by the dichroic mirror 34, it is condensed by the condensing lens 37, and is received by the photoelectric detection device 38. The photoelectric detection device 38 performs photoelectric conversion of the received fluorescence, and provides an electric signal obtained as a result to the generation unit 71 via the controller 15.

On the basis of the electric signal provided from the photoelectric detection device 38, the generation unit 71 generates the cell membrane image of the sample 17, and provides it to the control unit 73. The cell membrane image thus obtained is an image obtained by visualizing the cells of the observation target, and the generation unit 71 generates the cell membrane image for each well.

In step S12, the generation unit 71 obtains the tTJ image in accordance with the control of the control unit 73.

More specifically, the light source 11 emits illumination light to irradiate the sample 17 via the beam expander 12, and via the dichroic mirror 31 to the object lens 35. In this case, the illumination light is light having a wavelength different from that when the cell membrane image is obtained, which enables fluorescent observation of the protein (Y) localized at a portion where mainly three cells are in contact with each other (tTJ)

When the sample 17 is irradiated with the illumination light, the protein (Y) localized in the tTJ emits fluorescence, and this fluorescence is received by the photoelectric detection device 38 via the object lens 35, the dichroic mirror 34, and the condensing lens 37.

Then, the electric signal obtained from the photoelectric conversion by the photoelectric detection device 38 is provided via the controller 15 to the generation unit 71, and accordingly, on the basis of the electric signal, the generation unit 71 generates the tTJ image and provides it to the control unit 73. The tTJ image thus obtained is an image obtained by visualizing the protein (Y) localized in the tTJ of the cells of the observation target, and the generation unit 71 generates the tTJ image for each well.

Figure 4:
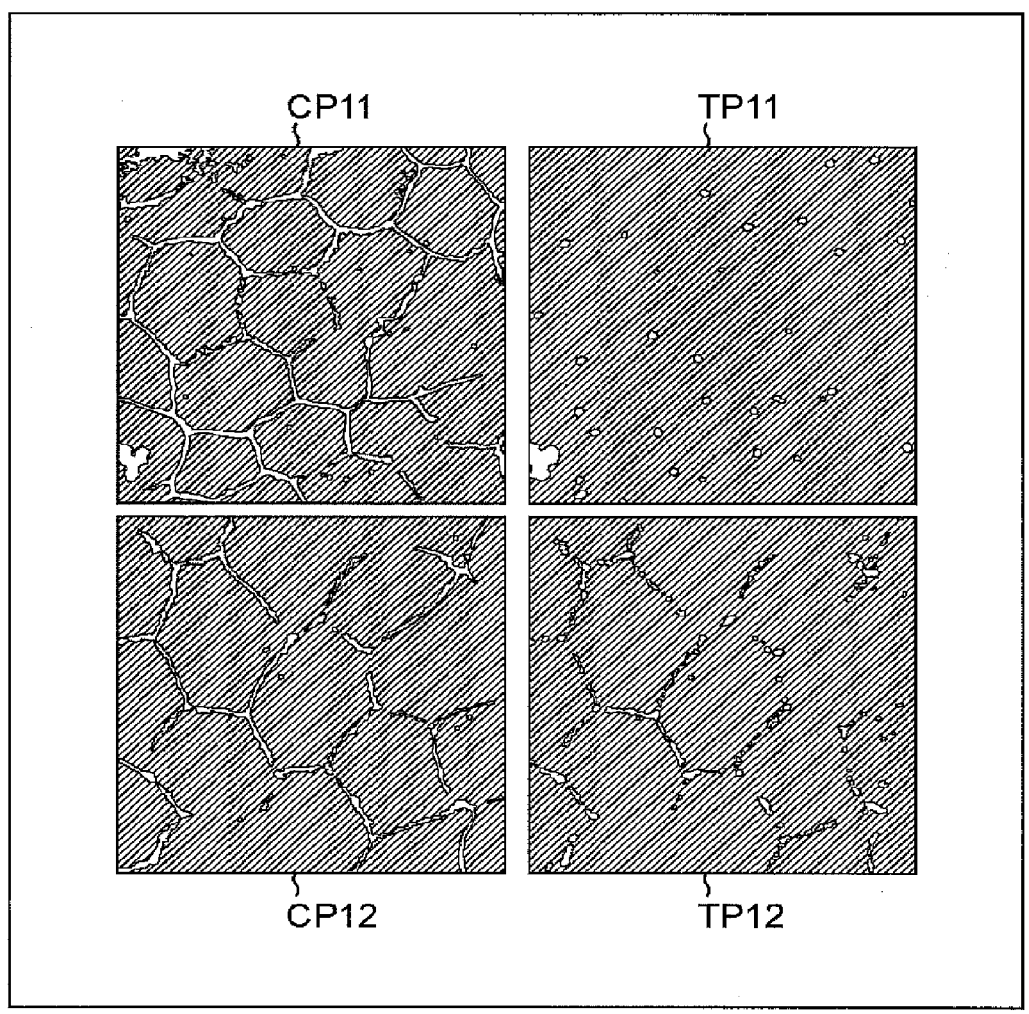
FIG. 4 is a figure illustrating an example of a cell membrane image and a tTJ image.

With the processing of steps S11 and S12 explained above, for example, the cell membrane image CP11 and the cell membrane image CP12, and the tTJ image TP11 and the tTJ image TP12 are obtained, as illustrated in FIG. 4.

The cell membrane image CP11 and the cell membrane image CP12 are cell membrane images of the cells observed under conditions different from each other, i.e., cell membrane images of wells different from each other, as illustrated in FIG. 4.

The tTJ image TP11 is a tTJ image of the observation target (well) that is the same as the cell membrane image CP11, and the tTJ image TP12 is a tTJ image of the observation target that is the same as the cell membrane image CP12. The cell membrane image CP11 and the tTJ image TP11 are the images of the same portion of the observation target, and the cell membrane image CP12 and the tTJ image TP12 are the images of the same portion of the observation target.

For example, in the cell membrane image CP11 and the cell membrane image CP12, a region with diagonal lines is a region inside of one cell, and a region without diagonal lines between the cells is a border region of the cells. More specifically, it is a region where the protein (X) localized at the cell membrane exists. In the tTJ image TP11 and the tTJ image TP12, a region without diagonal lines is a region where the protein (Y) localized in the tTJ exists, and a region with diagonal lines is a region (cell region) other than that.

In the tTJ image TP11, it is understood that, in the border portion of the cells as illustrated in the cell membrane image CP11, the protein (Y) is condensed in a portion where three cells are in contact with each other (tTJ) in particular. As described above, it is said that, when the protein (Y) is condensed in the tTJ, the adhesion strength of the cells is high, and the cells are adhered strongly with each other.

In contrast, in the tTJ image TP12, it is understood that the protein (Y) localized in the portion where three cells are in contact with each other (tTJ) leaks to the border portion of the cells as illustrated in the cell membrane image CP12. As described above, when the localization of the protein (Y) condensed at the tTJ changes, the adhesion strength of the cells is reduced.

Figure 3:
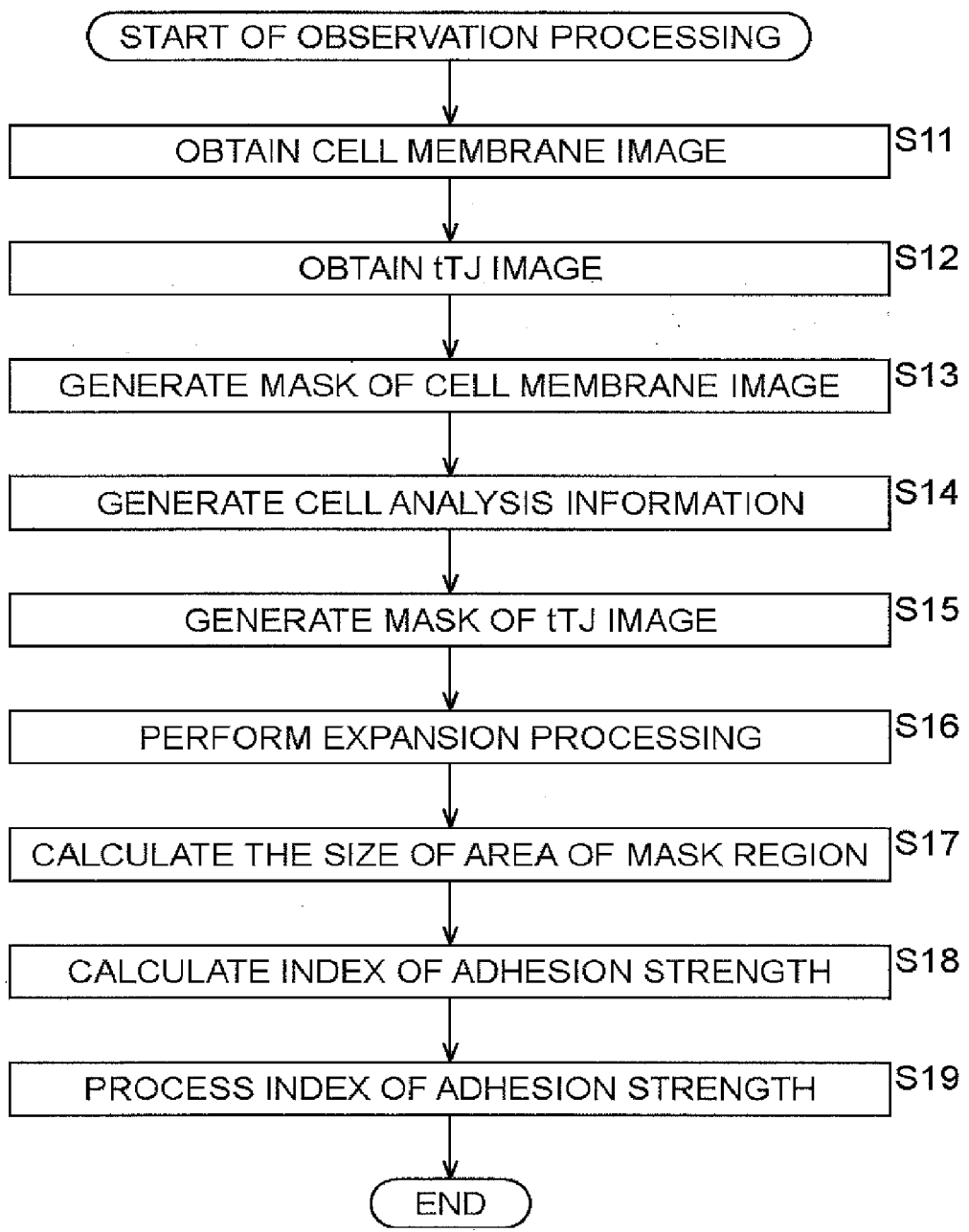
FIG. 3 is a flowchart for explaining observation processing.

Back to the explanation of the flowchart of FIG. 3, when the cell membrane image and the tTJ image are obtained the processing proceeds from step S12 to step S13.

In step S13, the cell membrane image processing unit 81 performs software matching and the like on the basis of the cell membrane image provided from the generation unit 71, and generates the mask of the cell membrane image.

For example, the control unit 73 provides the display unit 74 with the cell membrane image, and the cell membrane image is displayed. Then, the user operates the input unit 72 to designate, as the region which is to be the mask, the region of the protein (X) localized in the cell membrane on the cell membrane image displayed on the display unit 74, and designates, as the region which is not to be the mask, the region where there is no protein (X), i.e., the region in the cell.

When such input operation is performed, the cell membrane image processing unit 81 identifies, on the basis of the signal from the input unit 72, the brightness pattern of the region which is to be the mask on the cell membrane image (hereinafter referred to as mask region) and the region which is not to be the mask (hereinafter referred to as mask exclusion region). Then, the cell membrane image processing unit 81 performs segmentation of the region of the cell membrane on the basis of such brightness pattern, and generates a mask image indicating a mask region on the cell membrane image.

Figure 5:
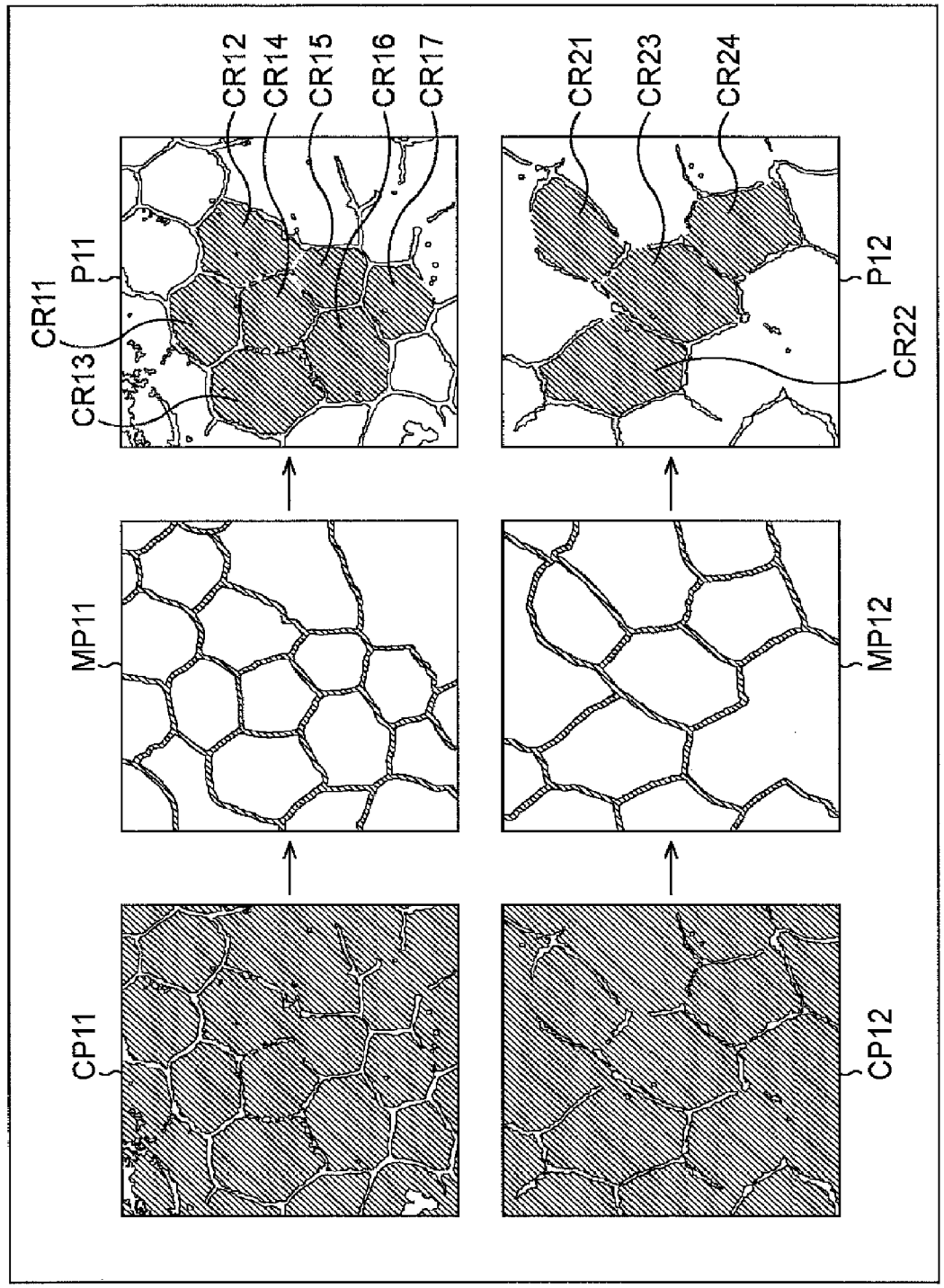
FIG. 5 is a figure for explaining generation of a cell mask image.

For example, suppose that the cell membrane image CP11 and the cell membrane image CP12 as illustrated in FIG. 5 are processing target. In FIG. 5, the same reference numerals are given to the portions corresponding to the case of FIG. 4, and the explanation thereabout is omitted as necessary.

In such case, first, the control unit 73 displays the cell membrane image CP11 on the display unit 74. The user designates, as the mask region, the region where diagonal lines are not attached in the cell membrane image CP11, i.e., the region of any given cell membrane, and designates, as the mask exclusion region, the region in any given cell with diagonal lines.

Then, the brightness patterns of the region with diagonal lines and the region without diagonal lines on the cell membrane image CP11 are identified, and the mask image MP11 is obtained, in which the region of the cell membrane designated as the mask region is shown. In the mask image MP11, the region with diagonal lines indicates the mask region, and this mask region is a border of cells.

Further, the cell membrane image processing unit 81 subtracts the mask region shown in the mask image MP11 from the original cell membrane image CP11, whereby the region of a cell (the inside of the cell) is extracted from the cell membrane image CP11. For example, the cell membrane image processing unit 81 derives the difference of the cell membrane image CP11 and the mask image MP11, whereby the cell mask image P11 showing the region of each cell (the inside of the cell) is generated. In the cell mask image P11, each of seven regions, i.e., the region CR11 to the region CR17, indicates a region of one cell (the inside of the cell).

Subsequently, the cell membrane image processing unit 81 performs the same processing as the case of the cell membrane image CP11 to generate the mask image MP12 by segmentation on the cell membrane image CP12, and generates the cell mask image P12 from the cell membrane image CP12 and the mask image MP12. In the cell mask image P12, each of four regions, i.e., the region CR21 to the region CR24, indicates a region of one cell (the inside of the cell).

When the mask image MP12 is generated, the user may designate the mask region and the mask exclusion region on the cell membrane image CP12, but when the mask image MP11 is generated, the brightness patterns of these regions are already identified, and therefore, designation operation by the user is not performed in particular.

The processing of the software matching explained above is described in detail in the specification of U.S. Pat. No. 7,203,360B2, for example.

Back to the flowchart of FIG. 3, after the cell mask image is generated for each cell membrane image, in step S14, the cell membrane image processing unit 81 generates cell analysis information including the number of cells recognized in the cell membrane image and the size of area of each cell on the basis of the generated cell mask image. The cell analysis information is generated for each cell membrane image.

For example, in the example of FIG. 5, information including the number of regions "7" of the cell extracted from the cell mask image P11 and the size of area of the region of these cells, i.e., each region of the region CR11 to the region CR17 is generated as cell analysis information of the cell mask image P11. In the explanation below, the size of area of the region of each cell included in the cell analysis information will also be referred to as cell area size CA.

In step S15, the tTJ image processing unit 82 performs processing such as software matching on the basis of the tTJ image provided from the generation unit 71, and generates the mask of the tTJ image. More specifically, the same processing as the processing of step S13 is performed to generate the mask image indicating the region where the protein (Y) localized in the tTJ exists in the tTJ image.

In step S16, the tTJ image processing unit 82 generates the expansion mask image by performing the expansion processing on the mask image generated from the tTJ image.

Figure 6:
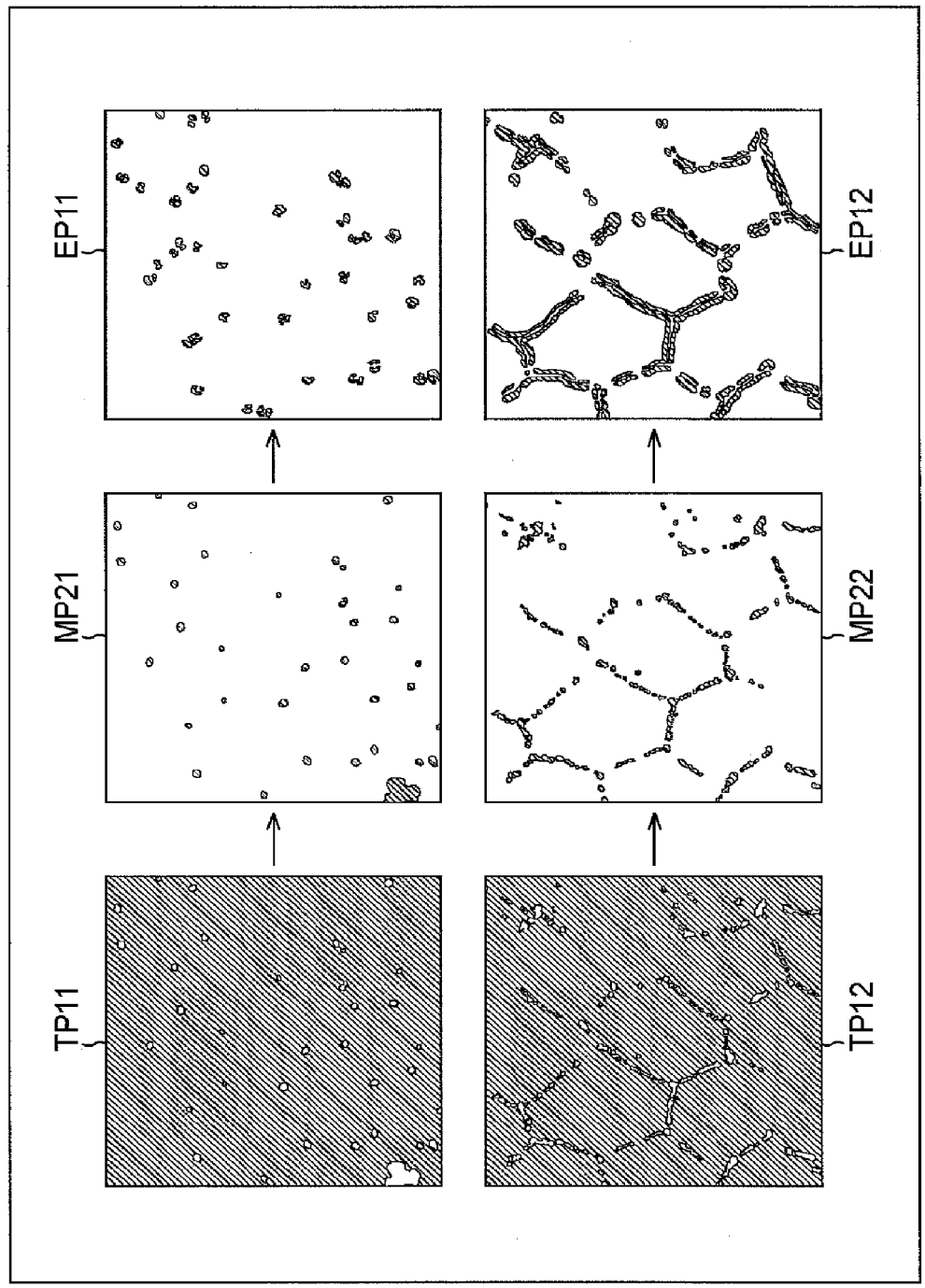
FIG. 6 is a figure for explaining generation of an expansion mask image.

For example, suppose that the tTJ image TP11 and the tTJ image TP12 as illustrated in FIG. 6 are processing target. In FIG. 6, the same reference numerals are given to the portions corresponding to the case of FIG. 4, and the explanation thereabout is omitted as necessary.

In such case, first, the control unit 73 displays tTJ image TP11 on the display unit 74. The user designates, as the mask region, the region where diagonal lines are not attached in the tTJ image TP11, i.e., the region of any given protein (Y) localized in the tTJ, and designates, as the mask exclusion region, the region in any given cell with diagonal lines.

Then, like the generation of the mask image of the cell membrane image, the brightness patterns of the mask region and the mask exclusion region are identified, and the mask image MP21 is obtained, which indicates the region of the protein (Y) designated as the mask region by segmentation. In the mask image MP21, the region with diagonal lines indicates the mask region.

Further, the tTJ image processing unit 82 performs expansion processing on the mask image MP21, and generates the expansion mask image EP11 which is obtained by expanding the mask region. For example, in the expansion processing, the tTJ image processing unit 82 expands, with a certain ratio, the mask region in the mask image MP21, i.e., the region with diagonal lines. In the expansion mask image EP11, the region with diagonal lines also indicates the mask region which is the region of the protein (Y) localized in the tTJ.

Like the case of the tTJ image TP11, the tTJ image processing unit 82 generates the mask image MP22 by segmentation on the tTJ image TP12, and further, generates the expansion mask image EP12 by expansion processing on the mask image MP22.

In step S17, for each of the cells included in the expansion mask image, the tTJ image processing unit 82 calculates the size of area of the mask region included in the cell.

For example, the tTJ image processing unit 82 identifies the region of each cell in the expansion mask image EP11 of FIG. 6 on the basis of the cell mask image P11 shown in FIG. 5. Then, the tTJ image processing unit 82 calculates the size of area of the mask region included in the region of the cell in the expansion mask image EP11 for each of the cells, i.e., the size of area (hereinafter also referred to as protein area size TA) of the region where the protein (Y) localized in the tTJ exists which is indicated with diagonal lines.

In the explanation, the region of each cell in the tTJ image is derived using the cell mask image. Alternatively, the region of each cell may be derived from the expansion mask image and the like. The region of the protein (Y) which is the mask region in the expansion mask image exists along the border of the cells, and therefore, the border of the cells are defined by connecting the mask regions in proximity, and the region of each cell can be identified.

In step S18, the calculation unit 83 calculates the index AD of the adhesion strength of the cells on the basis of a cell area size CA of each cell in the cell membrane image derived by the cell membrane image processing unit 81 and the protein area size TA of each cell on the tTJ image derived by the tTJ image processing unit 82.

For example, the calculation unit 83 calculates the following expression (1), and calculates the index AD for each cell included in each cell membrane image.

$$\text{index } AD = \text{protein area size } TA/\text{cell area size } CA \qquad (1)$$

In this case, the index AD is a value obtained by dividing the protein area size TA by the cell area size CA, and therefore, indicates the ratio of the region where the protein (Y) localized in the tTJ exists with respect to the entire region of the cell.

As described above, the more the protein (Y) is concentrated in the tTJ, the higher the adhesion strength of the cells is, and the protein (Y) leaks to the cell membrane, and the larger the size of area of the protein (Y) thereof is, the lower the adhesion strength of the cells becomes. Therefore, it can be said that, the smaller the value of the index AD of the cell is, the higher the adhesion strength of the cells thereof is.

In the explanation, when the protein area size TA is calculated, the mask region is expanded with a certain ratio in step S16. Alternatively, by performing the expansion processing, determination of the strength of the adhesion strength of the cells based on the index AD can be easily done.

More specifically, in the expansion processing, the region of the mask is expanded in accordance with the size of area of the region. Therefore, the size of area of the mask region is increased by a predetermined ratio of the original size of area of the mask region. Therefore, when the region where the protein (Y) localized in the tTJ exists is larger, the amount of increase of the index AD derived by performing the expansion processing with respect to the value of the index obtained without performing the expansion processing is higher. In other words, in a cell with a low degree of adhesion strength, the protein area size TA is amplified more greatly, and the difference between the index AD of a cell with a high degree of adhesion strength and the index AD of a cell with a low degree of adhesion strength is larger.

It should be noted that the index of the adhesion strength of the cells may be any index as long as it is calculated from quantitative information obtained from the cell membrane image and the tTJ image. For example, the value of cell area size CA-protein area size TA and the value of (cell area size CA-protein area size TA)/cell area size CA may be adopted as the index of the adhesion strength of the cells. The quantitative information obtained from the cell membrane image and the tTJ image is not limited to the size of area of the region of the protein and the size of area of the region of the cell, but the quantitative information may be size information about the region of the protein and size information about the region of the cell. For example, the size information of them may be any one of or a combination of the volume, the size of area of the surface, the size of area, the total length (the length of the entire periphery) of the contour of the region of the protein, the total length (the length of the entire periphery) of the contour of each cell, and the strength value.

In step S19, the processing unit 84 processes the index AD of the adhesion strength of the cells calculated by the calculation unit 83 as necessary, and provides the processing result to the display unit 74 to display the processing result thereon.

Figure 7:
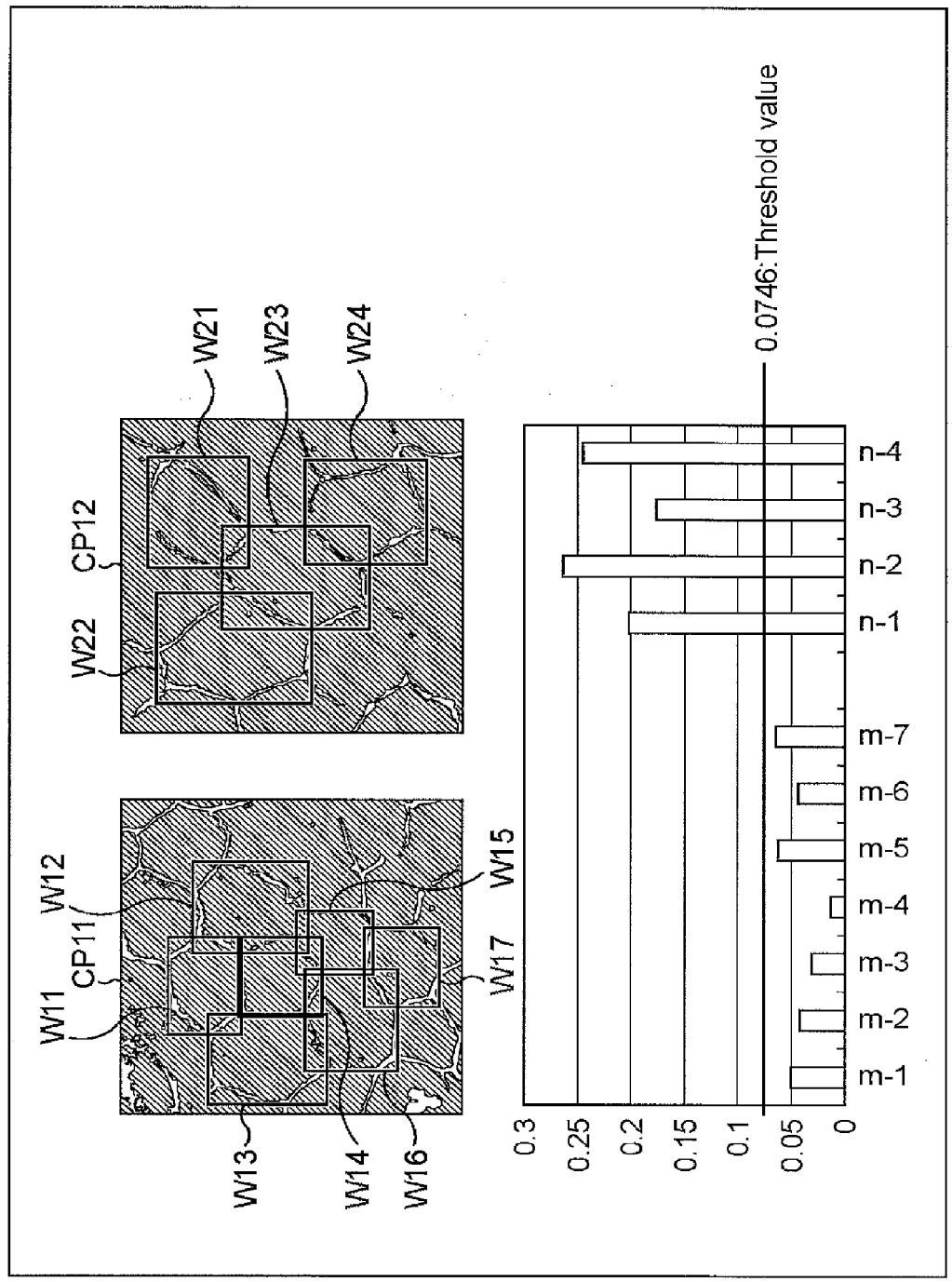
FIG. 7 is a figure illustrating an example of processing result of the index of adhesion strength of cells.

For example, as illustrated at the lower side of FIG. 7, the processing unit 84 generates a graph representing the index AD of the adhesion strength derived for each cell, and displays it on the display unit 74, and as illustrated at the upper side of the figure, the processing unit 84 processes the cell membrane image CP11 and the cell membrane image CP12, and displays it on the display unit 74. In FIG. 7, the same reference numerals are given to the portions corresponding to the case of FIG. 4, and the explanation thereabout is omitted.

In the graph as illustrated at the lower side of FIG. 7, the horizontal axis denotes the name given to each cell, and the vertical axis denotes the value of the index AD of the adhesion strength derived for each of the cells. The processing unit 84 assumes that a cell of which index value AD of adhesion strength is more than a predetermined threshold value th is a cell of which adhesion strength is low (weak), and a cell of which index value AD is less than or equal to the threshold value th is a cell of which adhesion strength is high (strong).

In the graph of FIG. 7, the threshold value th is "0.0746", and seven cells at the left side of the graph are cells having strong adhesion strength. These cells are cells included in, for example, the cell membrane image CP11. As a result of comparison with the threshold value th, four cells at the right side of the graph are cells of weak adhesion strength. These cells are cells included in, for example, the cell membrane image CP12.

The threshold value th may be directly designated by the user, or may be derived from calculation result and the like of the index AD for each cell. For example, the user may cause the tTJ image to be displayed, and designate cells of which adhesion strength is considered to be weak and cells of which adhesion strength is considered to be strong, and the threshold value th may be calculated from the indexes AD of the cells designated by the user.

Further, processing unit 84 processes the cell membrane image CP11 and the cell membrane image CP12 on the basis of the comparison result (the result of the threshold value processing) of the index AD and the threshold value th.

For example, as shown at the upper side in the figure, the processing unit 84 encircles each cell with a frame in the cell membrane image CP11, and displays the region in the frame in a display format according to the comparison result of the index AD and the threshold value th. In the cell membrane image CP11, each of the rectangular region W11 to the rectangular region W17 including each cell is displayed in a color indicating that each cell has high adhesion strength (for example, red).

Likewise, the processing unit 84 encircles each cell with a frame in the cell membrane image CP12, and displays the region in the frame in a display format according to the comparison result of the index AD and the threshold value th. In the cell membrane image CP12, each of the rectangular region W21 to the rectangular region W24 including each cell is displayed in a color indicating that each cell has low adhesion strength (for example, blue).

Figure 8:
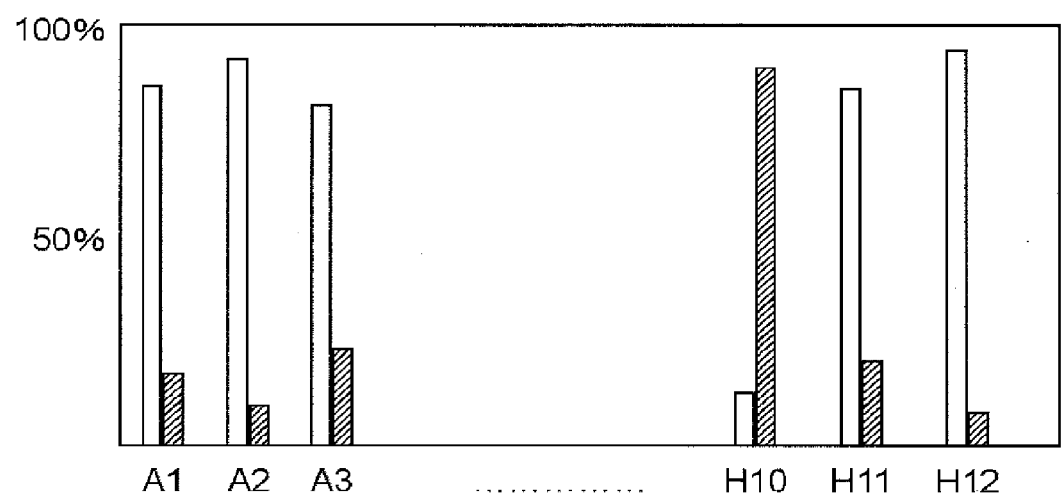
FIG. 8 is a figure illustrating an example of processing result of an index of adhesion strength of a cell.

In addition to the processing result as shown in FIG. 7, as shown in FIG. 8, the processing unit 84 may generate statistics information indicating strength determination result of adhesion of the cells included in the well for each well (observation condition), and may display the statistics information on the display unit 74.

In FIG. 8, the horizontal axis denotes the name given to each well, and the vertical axis denotes a ratio of a cell having high adhesion strength and a cell having low adhesion strength in each well.

For example, each of A1 to H12 as shown in the horizontal axis represents the name given to each well. The bar graph without diagonal lines in each well represents a ratio of the number of cells determined to have high adhesion strength with respect to the total number of cells included in the well. The bar graph with diagonal lines in each well represents a ratio of the number of cells determined to have low adhesion strength with respect to the total number of cells included in the well.

In the example of FIG. 8, in most wells, there are fewer cells having low adhesion strength, and most of the cells are cells having high adhesion strength, but in the well "H10", there are fewer cells having high adhesion strength, and most of the cells are cells having low adhesion strength. It is understood from this result that the effect of medicine is achieved under the observation condition of the well "H10".

It should be noted that the threshold value may be set by user's designation and the like, and when the ratio of the cells having low adhesion strength is equal to or more than the threshold value, the processing unit 84 may determine presence of the effect of the medicine. In this case, presence/absence of the effect of the medicine in each well can be quantitatively determined.

When the processing unit 84 processes and outputs the index AD of the adhesion strength as described above, the observation processing is finished.

As described above, the observation system obtains the cell membrane image and the tTJ image, derives the cell area size CA and the protein area size TA from these images, and derives the ratio as the index AD of the adhesion strength of each cell.

In the present embodiment, the cell membrane image and the tTJ image are obtained, and the cell area size CA and the protein area size TA are obtained from these images, but the present embodiment is not limited thereto. For example, the region where the protein (Y) localized in the tTJ exists may be identified from the tTJ image, and the region of the cell may be predicted (using publicly-known prediction means) and identified, and the cell area size CA and the protein area size TA may be derived, and the index AD of the adhesion strength may be calculated.

As described above, by deriving the index AD of the adhesion strength of each cell, the feature of particular cells, e.g., the degree of adhesion of the cells, can be quantitatively observed.

By processing the index AD of the adhesion strength derived for each cell as necessary and presenting the processing result thereof, it is possible to easily identify a condition under which the effect of the medicine can be achieved. More specifically, by analyzing individual cells with certain criteria, the effect of the medicine during medicine screening can be determined more efficiently. In particular, as compared to determination based on visual inspection which has been done in the past, determination and the like can be done objectively in a short time.

In the above explanation, for example, localization of the protein related to the adhesion strength of the cells is observed, and the index representing the adhesion strength is calculated as an index indicating the feature of the cell. Alternatively, a value representing the degree of activity of the cell may be calculated.

The series of processing explained above may be executed either by hardware or software. When the above series of processing is executed by software, a program constituting the software is read and recorded from a recording medium by, for example, the computer 16. Then, the program recorded in the computer 16 is executed by the computer 16, and the observation processing and the like of FIG. 3 is executed.

The embodiment of the present invention is not limited to the embodiment explained above. It may be changed in various manners without deviating from the gist of the present invention.

REFERENCE SIGNS LIST

13 scan head, 14 microscope, 16 computer, 17 sample, 71 generation unit, 73 control unit, 74 display unit, 81 cell membrane image processing unit, 82 tTJ image processing unit, 83 calculation unit, 84 processing unit

The invention claimed is:
1. An image processing apparatus comprising:
   a processor configured to:
      calculate quantitative information related to a region of at least one protein in a first observation image, and
      calculate, based on the calculated quantitative information related to the region of the at least one protein, an index representing an adhesion strength of at least one cell.

2. The image processing apparatus according to claim 1, wherein
the processor is further configured to:
calculate quantitative information related to a region of the at least one cell, and
calculate on the basis of the calculated quantitative information related to the region of the at least one protein, and the calculated quantitative information related to the region of the at least one cell, the index representing the adhesion strength of the at least one cell.

3. The image processing apparatus according to claim 2, wherein
the processor is further configured to calculate the index representing the adhesion strength of the at least one cell by calculating a ratio of the calculated quantitative information related to the region of the at least one protein and the calculated quantitative information related to the region of the at least one cell.

4. The image processing apparatus according to claim 1, wherein the first observation image is an observation image having the at least one protein localized in a tricellular tight junction of the at least one cell.

5. The image processing apparatus according to claim 1, wherein
the processor is further configured to determine whether the adhesion strength of the at least one cell is strong or weak based on the index representing the adhesion strength of the at least one cell.

6. The image processing apparatus according to claim 5, wherein
the processor is further configured to determine whether the adhesion strength of the at least one cell is strong or weak by comparing the index representing the adhesion strength of the at least one cell and a threshold value.

7. The image processing apparatus according to claim 5, wherein
the processor is further configured to control a display to display information related to a number of cells determined to have strong adhesion strength and/or a number of cells determined to have weak adhesion strength.

8. The image processing apparatus according to claim 5, wherein
the processor is further configured to determine an effect of medicine based on information related to a number of cells determined to have strong adhesion strength and/or a number of cells determined to have weak adhesion strength.

9. The image processing apparatus according to claim 1, wherein the processor is further configured to:
generate a graph representing the index of the adhesion strength of the at least one cell, and
control a display to display the generated graph representing the adhesion strength of the at least one cell.

10. The image processing apparatus according to claim 2, wherein
the processor is further configured to calculate the quantitative information related to the region of the at least one cell based on a second observation image.

11. The image processing apparatus according to claim 10, wherein
the first observation image is an image captured with irradiation of a light having a first wavelength on the at least one protein, and
the second observation image is an image captured with irradiation of a light having a second wavelength on the at least one cell.

12. A microscope system comprising:
an object lens;
an imaging apparatus configured to capture a plurality of well images of a plurality of wells; and
a processor configured to:
for each well image of the plurality of well images captured by the imaging apparatus:
calculate quantitative information related to a region of at least one protein in the well image,
calculate an index representing an adhesion strength of at least one cell in the well image based on the calculated quantitative information related to the region of the at least one protein in the well image, and
determine an effect of medicine based on the index representing the adhesion strength of the at least one cell in the well image.

13. A microscope system comprising:
an object lens;
an imaging apparatus configured to capture a plurality of well images of a plurality of wells;
a display; and
a processor configured to:
for each well image of the plurality of well images captured by the imaging apparatus:
calculate quantitative information related to a region of at least one protein in the well image,
calculate an index representing an adhesion strength of at least one cell in the well image based on the calculated quantitative information related to the region of the at least one protein in the well image,
determine whether the adhesion strength of the at least one cell in the well image is strong or weak based on the index representing the adhesion strength of the at least one cell in the well image, and
control the display to display information related to a number of cells in the well image determined to have strong adhesion strength and/or a number of cells in the well image determined to have weak adhesion strength.

14. The microscope system according to claim 13, wherein
the processor is further configured to, for each well image, determine an effect of medicine based on the information related to the number of cells of the well image determined to have strong adhesion strength and/or the number of cells of the well image determined to have weak adhesion strength.

15. An image processing apparatus comprising:
a processor configured to:
calculate information related to a size of a region of at least one protein in a first observation image, and
calculate, based on the calculated information related to the size of the region of the at least one protein, an index representing adhesion strength of at least one cell.

16. The image processing apparatus according to claim 15, wherein the processor is further configured to:
calculate information related to a size of a region of the at least one cell, and
calculate, based on the calculated information related to the size of the region of the at least one protein and the calculated information related to the size of the region of the at least one cell, the index representing the adhesion strength of the at least one cell.

17. The image processing apparatus according to claim 16, wherein
the processor is further configured to calculate the index representing the adhesion strength of the at least one cell by calculating a ratio of the calculated information related to the size of the region of the at least one protein and the calculated information related to the size of the region of the at least one cell.

18. The image processing apparatus according to claim 15, wherein the first observation image is an observation image having the at least one protein localized in a tricellular tight junction of the at least one cell.

19. The image processing apparatus according to claim 15, wherein
the processor is further configured to determine whether the adhesion strength of the at least one cell is strong or weak based on the index representing the adhesion strength of the at least one cell.

20. The image processing apparatus according to claim 19, wherein
the processor is further configured to determine whether the adhesion strength of the cell is strong or weak by comparing the index representing the adhesion strength of the at least one cell and a threshold value.

21. The image processing apparatus according to claim 19, wherein
the processor is further configured to control a display to display information related to a number of cells determined to have strong adhesion strength and/or a number of cells determined to have weak adhesion strength.

22. The image processing apparatus according to claim 19, wherein
the processor is further configured to determine an effect of medicine based on information related to a number of cells determined to have strong adhesion strength and/or a number of cells determined to have weak adhesion strength.

23. The image processing apparatus according to claim 15, wherein the processor is further configured to:
generate a graph representing the index of the adhesion strength of the at least one cell, and
control a display to display the generated graph representing the adhesion strength of the at least one cell.

24. The image processing apparatus according to claim 16, wherein
the processor is further configured to calculate the information related to the size of the region of the at least one cell based on a second observation image.

25. The image processing apparatus according to claim 24, wherein
the first observation image is an image captured with irradiation of a light having a first wavelength on the at least one protein, and
the second observation image is an image captured with irradiation of a light having a second wavelength on the at least one cell.

26. A microscope system comprising:
an object lens;
an imaging apparatus configured to capture a plurality of well images of a plurality of wells; and
a processor configured to:
for each well image of the plurality of well images captured by the imaging apparatus:
calculate information related to a size of a region of at least one protein in the well image,
calculate an index representing an adhesion strength of at least one cell in the well image based on the calculated information related to the size of the region of the at least one protein in the well image, and
determine an effect of medicine based on the index representing the adhesion strength of the at least one cell in the well image.

27. A microscope system comprising:
an object lens;
an imaging apparatus configured to capture a plurality of well images of a plurality of wells;
a display; and
a processor configured to:
for each well image of the plurality of well images captured by the imaging apparatus:
calculate information related to a size of a region of at least one protein in the well image,
calculate an index representing an adhesion strength of at least one cell in the well image based on the calculated information related to the size of the region of the at least one protein in the well image,
determine whether the adhesion strength of the at least one cell in the well image is strong or weak based on the index representing the adhesion strength of the at least one cell in the well image, and
control the display to display information related to a number of cells in the well image determined to have strong adhesion strength and/or a number of cells determined to have weak adhesion strength.

28. The microscope system according to claim 27, wherein
the processor is configured to, for each well image, determine an effect of medicine based on the information related to the number of cells of the well image determined to have strong adhesion strength and/or the number of cells of the well image determined to have weak adhesion strength.

29. An image processing apparatus comprising:
a processor configured to:
calculate information related to an area of at least one protein in a first observation image, and
calculate, based on the calculated information related to the area of the at least one protein, an index representing adhesion strength of at least one cell.

30. The image processing apparatus according to claim 29, wherein
the processor is further configured to:
calculate information related to an area of the at least one cell, and
calculate, based on the calculated information related to the area of the at least one protein, and the calculated information related to the area of the at least one cell, the index representing the adhesion strength of the at least one cell.

31. The image processing apparatus according to claim 30, wherein
the processor is further configured to calculate the index representing the adhesion strength of the at least one cell by calculating a ratio of the calculated information related to the area of the at least one protein and the calculated information related to the area of the at least one cell.

32. The image processing apparatus according to claim 29, wherein the first observation image is an observation image having the at least one protein localized in a tricellular tight junction of the at least one cell.

33. The image processing apparatus according to claim 29, wherein
the processor is further configured to determine whether the adhesion strength of the at least one cell is strong or weak based on the index representing the adhesion strength of the at least one cell.

34. The image processing apparatus according to claim 33, wherein
the processor is further configured to determine whether the adhesion strength of the at least one cell is strong or weak by comparing the index representing the adhesion strength of the at least one cell and a threshold value.

35. The image processing apparatus according to claim 33, wherein
the processor is further configured to control a display to display information related to a number of cells determined to have strong adhesion strength and/or a number of cells determined to have weak adhesion strength.

36. The image processing apparatus according to claim 33, wherein
the processor is further configured to determine an effect of medicine based on information related to a number of cells determined to have strong adhesion strength and/or a number of cells determined to have weak adhesion strength.

37. The image processing apparatus according to claim 29, wherein the processor is further configured to:
generate a graph representing the index of the adhesion strength of the at least one cell, and
control a display to display the generated graph representing the adhesion strength of the at least one cell.

38. The image processing apparatus according to claim 30, wherein
the processor is further configured to calculate the information related to the area of the at least one cell based on a second observation image.

39. The image processing apparatus according to claim 38, wherein
the first observation image is an image captured with irradiation of a light having a first wavelength on the at least one protein, and
the second observation image is an image captured with irradiation of a light having a second wavelength on the at least one cell.

40. A microscope system comprising:
an object lens;
an imaging apparatus configured to capture a plurality of well images of a plurality of wells; and
a processor configured to:
for each well image of the plurality of well images captured by the imaging apparatus:
calculate information related to an area of at least one protein in the well image,
calculate an index representing an adhesion strength of at least one cell in the well image based on the calculated information related to the area of the at least one protein in the well image, and
determine an effect of medicine based on the index representing the adhesion strength of the at least one cell in the well image.

41. A microscope system comprising:
an object lens;
an imaging apparatus configured to capture a plurality of well images of a plurality of wells;
a display; and
a processor configured to:
for each well image of the plurality of well images captured by the imaging apparatus:
calculate information related to an area of at least one protein in the well image,
calculate an index representing an adhesion strength of at least one cell in the well image based on the calculated information related to the area of the at least one protein in the well image,
determine whether the adhesion strength of the at least one cell in the well image is strong or weak based on the index representing the adhesion strength of the at least one cell in the well image, and
control the display to display information related to a number of cells in the well image determined to have strong adhesion strength and/or a number of cells in the well image determined to have weak adhesion strength.

42. The microscope system according to claim 41, wherein
the processor is further configured to, for each well image, determine an effect of medicine based on the information related to the number of cells in the well image determined to have strong adhesion strength and/or the number of cells in the well image determined to have weak adhesion strength.

* * * * *